United States Patent [19]

Dodin et al.

[11] Patent Number: 4,898,815

[45] Date of Patent: Feb. 6, 1990

[54] NOVEL SYNTHETIC PEPTIDE, PROCESS FOR ITS PREPARATION AND MEDICAMENTS CONTAINING IT

[75] Inventors: Andre Dodin, Milly La Foret; Odile Siffert, Versailles; Georgette Le Thuillier, Morangis; Patrice Allard, Paris, all of France

[73] Assignee: Institut Pasteur, Paris, France

[21] Appl. No.: 4,416

[22] Filed: Jan. 20, 1987

Related U.S. Application Data

[62] Division of Ser. No. 643,955, Aug. 24, 1984, Pat. No. 4,686,281.

[30] Foreign Application Priority Data

Aug. 29, 1983 [FR] France ................................ 83 13828

[51] Int. Cl.$^4$ ..................... G01N 33/569; A61K 39/40
[52] U.S. Cl. ......................................... 435/7; 435/810; 424/87; 530/387
[58] Field of Search ................. 435/7, 34, 38, 39, 810; 424/87; 530/327, 387, 328–330

[56]   References Cited

U.S. PATENT DOCUMENTS 4,499,080   2/1985   Duflot et al. ........................ 530/327

OTHER PUBLICATIONS

Spicer et al, J. Biol. Chem., 257(10): 5716–5721, "Escherichia coli Heat Labile Enterotoxin", (1982, May).
Spicer et al, Proc. Nat'l. Acad. Sci. USA, 78(1): 50–54, "Sequence Homologies between A Subunits of *Escherichia coli* and *Vibrio cholerae* Enterotoxins", (1981).
Lindholm et al, Inf. Immun., 40(2): 570–576, "Monoclonal Antibodies to Cholera Toxin with Special Reference to Cross–Reactions with *E. coli* Heat Labile Enterotoxin", (May, 1983).
Robb et al, Inf. Immun., 38(1): 267–272, "Isolation of Hybridoma Cell Lines and Characterization of Monoclonal Antibodies Against Cholera Exterotoxin and its Subunits", (1982).
Clements et al., Inf. Immun., 21(3): 1036–1039, "Immunological Cross–Reactivity between a Heat–Labile Enterotoxin(s) of *E. coli* and Subunits of *V. Choleare* Enterotoxin", (1978).

Primary Examiner—Esther M. Kepplinger
Attorney, Agent, or Firm—Oblon, Spivak, McClelland, Maier & Neustadt

[57]   ABSTRACT

The invention provides a synthetic peptide which reproduces at least 5 of the 11 amino acids common to the γ chain of sub-unit A of cholera toxin and the γ chain of LT toxin of *Escherichia coli*. It is preferably constituted by a pentadecapeptide which corresponds to the following formula (I):

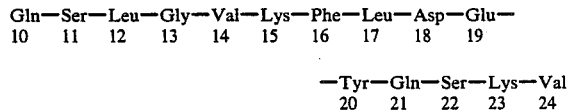

The process of synthesis is by the step by step construction of the peptide chain starting from the C terminal end of said chain, by the successive fixing of the amino acids which constitute the latter. A novel medicament for the treatment of cholera and infectious gastro-enterites comprises said synthetic peptide as active constituent. A diagnosis agent for cholera and/or infectious gastro-enterites comprises a sequence of nucleotides corresponding to the 5 minimum amino acids of the synthetic peptide.

6 Claims, 1 Drawing Sheet

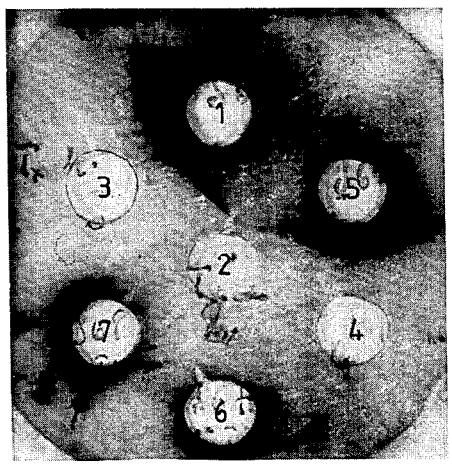

NOVEL SYNTHETIC PEPTIDE, PROCESS FOR ITS PREPARATION AND MEDICAMENTS CONTAINING IT

This is a division of application Ser. No. 643,955, filed Aug. 24, 1984 now U.S. Pat. No. 4,686,281.

BACKGROUND OF THE INVENTION

1. Field of the Invention

The present invention relates to a novel peptide which comprises a sequence of amino acids reproducing more particularly the interaction site between sub-unit A and sub-unit B of cholera toxin.

2. Description of the Background

As is known [Cf. J. HOLMGREN, NATURE, 292, 30 July 1981, p. 413–417] the watery diarrhea characteristic of cholera which, if it is not arrested, leads to dehydration, to metabolic acidosis and death, is due to the cholera toxin secreted by *Vibrio cholerae.* The mechanism of action of cholera toxin is well known; it fixes itself to receptors which are present on the mucous cells and stimulates intestinal adenyl cyclase activity, which has the effect of increasing the cyclic A.M.P. level present in the cells of the small intestine; the latter causes diarrhea and fluid loss through severe water depletion and inhibition of the absorption of sodium chloride by the intestinal villosities and by the stimulation of the active secretion of chlorine by the cryptic cells.

It is also known that cholera toxin (cf) is a protein constituted of two polypeptide fragments: sub-unit B itself comprising five identical units, and sub-unit A [Cf. R. A. FINKELSTEIN, M. K. LARUE and J. J. LOSPALLUTO, INFECT. IMMUN., 6, 1972, pp 934]. It is accepted [Cf. J. HOLMGREN, Loc.quoted above] that the injurious action of the cholera toxin is manifested by the following facts: fixation of the sub-unit B of the toxin to the GM1 receptor of the membrane of the duodenal enterocyst, followed by an increase of the cyclic A.M.P. level due to an irreversible activation of the adenyl cyclase [Cf. D.M. GILL, ADV. CYCLIC NUCLEOTIDE RES., 8, 1977, pp. 85] which would lead one to think that the symptomatology of cholera arises from the introduction of the sub-unit A into the cell.

This sub-unit A has a hydrophobic character which is demonstrated when it is fractionated from the cholera toxin (CT), by reduction of the disulfide bridge, to give non-identical sub-units $\alpha$ and $\gamma$. According to W. H. J. WARD, P. BRITTON and S. VAN HEYNINGEN, (BIOCHEM. J., 199, 1981, pp 457), the $\alpha$ fragment would not have hydrophobic regions and, on the other hand, the $\gamma$ fragment would have an amphiphilic character, the hydrophobic regions being maskable in the intact sub-unit A. Finally, it would be due to the conductive fragment $\gamma$, that the $\alpha$ fragment would penetrate through the membrane of the cell. This is why, it appeared interesting and useful to Applicants to seek in the structure of the sub-unit A, the amino acid sequences responsible for the biological activities of the cholera toxin.

In addition, the investigations of E. K. SPICER, W. H. KAVANAUGH, W. S. DALLAS, S. FALKOW, W. H. KONIGSBERG and D. E. SCHAFER, reported in PROC. NATL. ACAD. SCI. U.S.A., 78, January 1981, p. 50–54 and those of W. S. DALLAS and S. FALKOW (NATURE, 288, 4 December 1980, p. 499–501) have demonstrated the existence of similarities of primary structure between the cholera toxin (CT) and the thermolabile enterotoxin of *Escherichia coli* (LT) responsible for infectious gastro-enterites: the cholera toxin CT and the thermolabile toxin LT of *Escherichia coli* are similar enterotoxins from the functional, structural and immunological point of view. They both cause elevation of the cyclic A.M.P. levels in the epithelial cells of the intestines by catalysing NAD-dependant ADP-ribosylation of the membranal proteins. They are both composed of two dissimilar sub-units, namely sub-unit A of enterotoxin which has an enzymatic activity and is the activator component of adenyl cyclase and the sub-unit B which recognizes the membranal components and fixes the holotoxin to the target cell, juxtaposing the sub-unit A with its substrates. It has been demonstrated that the membranal receptors of the sub-unit B of the cholera toxin and of the *Escherichia coli* toxin are similar but not identical, and that the monosialosylganglioside GM1 is the receptor of the CT and constitutes probably a portion of the receptor of the LT. It has been demonstrated [Cf. CL GYLES and D. A. BARNUM, J. INFECT. DIS., 120, p. 419–426 (1978)] that the LT and the CT are similar from the immunological point of view and that both their sub-units A and their sub-units B have common antigenic determinants [cf. J. D. CLEMENTS and R. A. FINKELSTEIN, INFECT. IMMUN., 21, p. 1036–1039 (1978)]. The primary structure of the sub-units B of the LT and of the CT has been determined and has shown that they have a homologous sequence of amino acids. The studies of SPICER et al and DALLAS et al mentioned above, have shown that there exists also similarities of primary structure and of their immunological properties between the sub-units A of the CT and of the LT and although the sequences of amino acids of these two sub-units are only partially identified at this time, it is however known that according to the studies of DUFFY and LAI [BIOCHEM. BIOPHYS. RES. COMM.,91, 1979, pp. 1005] the sub-unit A of the CT has a molecular weight of 29500, of which 24000 for the $\alpha$ chain and 5500 for the $\gamma$ chain whose composition in amino acids is known, which comprises 46 amino acids 11 of which are common with the $\gamma$ chain of the LT.

By taking stand on the hypothesis according to which the site of interaction between the sub-unit A and the sub-unit B of the CT would be localized in the $\gamma$ chain and more particularly in the sequence corresponding to the amino acids bearing numbers 10 to 24 from the terminal N of the latter, and by taking stand on the functional, structural and immunological similarity between the LT and the CT, Applicants considered that if they arrived at synthesizing a polypeptide having this sequence 10–24, they could obtain a protective agent both against cholera and against infectious gastro-enterites.

SUMMARY OF THE INVENTION

Accordingly the present invention provides a peptide reproducing at least 10 amino acids of the $\gamma$ chain of the sub-unit A of the cholera toxin common with the $\gamma$ chain of the LT toxin of *E. coli* or a peptide which can induce (alone or coupled with an immunogenic molecule such as a protein like bovine serumalbumin, for example) after injection in an animal, antibodies recognizing the common sequence such as defined above, or its equivalent, since it is, in fact, known that certain amino acids can be replaced by others without the secondary structure being notably modified.

DESCRIPTION OF THE PREFERRED EMBODIMENTS

Preferably, the present invention proposes to provide a pentadecapeptide reproducing the sequence 10-24 of the γ chain of the sub-unit A of the cholera toxin and having 5 amino acids common with the γ chain of the sub-unit A of the *Escherichia coli* toxin, which can serve as a protective agent, and particularly as a vaccine, at least against cholera and preferably both against cholera and against infectious gastro-enterites. This pentadecapeptide can be reproduced, according to the invention, by chemical synthesis or by any other means, such as the use of bacteria transformed by vectors bearing a sequence of nucleotides corresponding to the amino acids.

According to the present invention there is provided a peptide characterized in that it comprises at least 5 amino acids of the γ chain of the sub-unit A of cholera toxin common with the chain γ of the LT toxin of *Escherichia coli*.

According to a preferred embodiment of the invention, the latter provides a synthetic pentadecapeptide characterized in that it comprises the following formula I:

Gln—Ser—Leu—Gly—Val—Lys—Phe—Leu—Asp—Glu—
10   11   12   13   14   15   16   17   18   19

—Tyr—Gln—Ser—Lys—Val
20   21   22   23   24 which formula corresponds to the sequence 10-24 of the γ chain of the sub-unit A of cholera toxin and has 5 of the 11 amino acids common with the γ chain of the sub-unit A of the thermolabile toxin LT of *Escherichia coli*.

Study of the secondary structure of the γ chain of the sub-unit A of CT, made by the method of CHOU and FASMAN[ADVANCES IN ENZYMOL., 47, 1978, pp. 45] has shown that there exist two regions having a helical structure; the first is situated between the positions 5 and 12 and the second between the positions 15 and 24. These two regions are hydrophilic [according to the method of HOPP and WOODS (PROC. NATL. ACAD. SCI. U.S.A., 78, 1981, p. 3824] and represent a portion of the sequence having amino acids common with the LT.

According to the present invention there is also provided a process for the synthesis of the peptide comprising at least 5 of the 11 amino acids common to the γ chain of the sub-unit A of cholera toxin and to the γ chain of the LT toxin of *Escherichia coli*, which is characterized in that said peptide is synthesized by construction of the peptide chain step by step, starting from the C terminal end of said chain, by successive fixation of the amino acids which constitute the latter.

According to a preferred embodiment of the process according to the present invention, applied to the synthesis of the pentadecapeptide of formula I defined above, the latter is synthesized by construction of the peptidic chain step by step, starting from the C terminal end, that is to say starting from valine, by successive fixation of the amino acids which constitute the peptide chain.

According to another preferred embodiment of the process of synthesis according to the present invention, the latter is carried out in the solid phase, in the presence of a suitable coupling agent.

According to still another preferred modality of this embodiment, the synthesis in the solid phase is carried out by using a solid support constituted by a resin, preferably a chloromethylated resin or a phenolic resin, more particularly.

According to yet another preferred embodiment of the method of synthesis according to the invention, the α-amino function of the amino acids successively fixed to form the desired peptidic chain, is temporarily protected by a t-butoxycarbonyl group (Boc).

According to yet another preferred embodiment of the process of synthesis according to the invention, the side functions of the amino acids successively fixed to form desired the peptidic chain, are protected until the end of the synthesis by benzyl groups.

According to an advantageous feature of this embodiment, the carboxyl groups of the aspartic and glutamic acids are protected by benzyl ester groups.

According to another advantageous feature of this embodiment, the hydroxyl group of the serine is protected by a benzylether group.

According to still another advantageous feature of this embodiment, the ε amine of lysine is protected by a carbobenzyloxy group (CBZ).

According to a preferred embodiment of the process of synthesis according to the invention, the coupling agent employed to effect the step by step construction of the peptidic chain, is an equimolecular mixture of dicyclohexylcarbodiimide and 1-hydroxybenzotriazole in a suitable solvent, such as, more particularly, dimethylformamide or methylene chloride.

According to another preferred embodiment of the process of synthesis according to the invention, the protective group Boc of the α-amine function of the amino acids successively fixed, is removed by acidolysis.

According to yet another preferred embodiment of the process of synthesis according to the invention, the protective groups of the side functions of the amino acids successively fixed to form the desired peptidic chain, are removed and the terminal C function is simultaneously released once the synthesis is terminated, by the action of a strong acid, such as, more particularly, liquid hydrofluoric acid.

According to another preferred embodiment of the process of synthesis according to the invention, the free peptide obtained after removal of the protective groups, is purified by passage over at least one column of suitable molecular sieve, then purification by high performance liquid phase chromatography.

The present invention also provides a protective agent against cholera and/or infectious gastro-enterites, taken from the group which comprises serums and vaccines administrable parenterally, sub-cutaneously, cutaneously or orally, characterized in that it comprises the synthetic pentadecapeptide of the above-defined formula I.

According to an advantageous embodiment of the protective agent according to the present invention, the latter comprises said synthetic pentadecapeptide of formula I associated with a sub-unit B of cholera toxin and/or with a sub-unit B of the *Escherichia coli* toxin.

The present invention also relates to a novel medicament characterized in that it comprises, as active constituent a peptide according to the invention and particularly, the above-defined pentadecapeptide of formula I, said novel medicament being adapted to treat diseases connected with an activation of the adenylcyclase-cyclic AMP system.

In accordance with the present invention, the synthetic peptide can be used as an agent for the diagnosis of cholera and/or gastro-enterites.

According to an other advantageous modality of invention, the diagnostic agent comprising said synthetic peptide is advantageously constituted by a serum.

In accordance with the invention, a serum obtained from the synthetic peptide according to the invention is adapted to be used as a diagnosis agent of the presence of toxinogenic *Escherichia coli* (responsible for infectious gastro-enterites).

Also according to the invention, such a serum useful as a diagnostic agent of germs responsible for infectious gastro-enterites, is constituted by serum coming from rabbits previously treated with the synthetic peptide according to the invention.

The serum obtained according to the present invention is used as a diagnostic agent in a detection test of the presence of germs responsible for gastro-enterites, which consists in placing said diagnosis agent in contact with a biological medium (strain of the germ isolated on gelose, stools, urine or blood from the subject which is assumed to be contaminated or contaminated water), for a suitable time, of the order of 16 hours to 24 hours, but preferably for 18 hours, after which the appearance of a strip of antigen-antibody precipitate demonstrates the presence of said germs.

This diagnostic test is of great sensitivity, since it enables the detection of the presence of pathogenic germs in patient carrying a small amount of these germs, in very small quantities of biological media, which is added to the fact that this test only requires a very short time, since it suffices for 18 hours on the average for the strip of antigen-antibody precipitate which indicates the presence of pathogenic germs to reveal itself, whereas the diagnosis tests for the detection of the presence of toxinogenic *Escherichia coli* known in the prior art require 5 days and are very expensive relative to the diagnosis test according to the present invention.

For carrying out this diagnosis test there is provided, according to the present invention, a ready-for-use diagnosis kit which comprises a suitable amount of the peptide according to the invention as well as a suitable amount of anti-peptide antibody according to the invention, as reference standard, the reference standard being advantageously constituted by a suitable amount of anti-peptide 10-24 antibody.

The synthesis of the pentadecapeptide of formula I, according to the present invention, will be described below in the example which follows, which is given purely by way of illustration and is of no limiting character.

DESCRIPTION OF A PREFERRED EMBODIMENT

The method of synthesis employed is a method in solid phase for the synthesis of peptides derived from the method of R.B. MERRIFIELD [J.AMER. CHEM. SOC., 85, 1963, p. 2149].

The construction of the peptidic chain is effected by starting from the C terminal end which, in the present case, is valine, by successive fixing of amino acids, according to the step by step method.

The starting material is 1.5 g of chloromethylated resin "Bio Beads S - XI" (of BIO-RAD) of a capacity of 1.34 milliequivalents/gram of grain-size: 200–400 mesh, on which the valine is fixed in the form of Boc-valine per gram of resin; 1.85 g of substituted resin-valine at 0.46 mM/g, namely 0.69 mM per 1.85 g (GISIN Test) is obtained. The coupling of the successive amino acids is effected with an excess, preferably double the amount, with respect to the substitution, namely:

| | |
|---|---|
| Boc-amino acid | 1.4 mmole, |
| by using a coupling agent | |
| Hydroxybenzotriazole | 1.4 mmole |
| Dicyclohexylcarbodiimide | 1.4 mmole | in methylene chloride and/or dimethyl-formamide solvents.

The α-amino function of the amino acids is protected temporarily, at the moment of fixing the amino acid, by a Boc group, whilst the lateral functions are protected by the benzyl ester group for the acid functions, by the benzyl ether group for the alcohol functions and by the carbobenzyloxy group the ε amine of lysine.

The coupling and unblocking checks are carried out by the ninhydrin test (KAISER Test).

The Boc group is removed by acidolysis by means of 30% trifluoracetic acid in dichloromethane, and the other groups, including the C terminal function, are freed at the end of synthesis, by the action of liquid hydrofluoric acid.

The free peptide is purified by successive passages over molecular sieve columns, namely:

"ULTROGEL ACA 201". Elution by 0.1M acetic acid (Trademark belonging to L.K.B.)

"BIOGEL P4". Elution by 1M acetic acid (Trademark of BIORAD)

"BIOGEL P4". Elution by 0.1M acetic acid (Trademark of BIORAD)

The analyses of amino acids of the various fractions have permitted the desired peptide to be isolated, and it is finally purified by high performance liquid phase chromatography (HPLC) on a reverse phase column under the following conditions: "LICHROSORB" RB 18 column(Trademark registered by MERCK)(5 μm) 250 mm×4 mm. Eluent A: acetonitrile; Eluent B: $KH_2PO_4$, $5 \times 10^{-3}$M (pH=6.0; flow rate: 1.5 ml/min). Linear gradient of 20 to 80% of A in 30 minutes. UV detection at 220 nm, 0.02 full scale optical density unit. The purity of the product (TR:7.18 min) was 94%, under deduction of the surface of the peaks due to the solvent (T.R.<2.50 minutes).

BIOLOGICAL PROPERTIES OF THE SYNTHETIC 10-24 SEQUENCE

The biological activities of the complete cholera toxin are extremely varied; they are summarized in the enzymatic activities having as a mediator cyclic A.M.P.. The immunogenic character of the synthetic peptide 10-24 has been demonstrated by proceding as follows:

EQUIPMENT AND METHOD:

Rabbits were immunized with the synthetic peptide according to the invention, by the technique of OUDIN (1st injection, synthetic toxin, 100 mcg, +FREUND adjuvant intradermally, thereafter every 4 days, an intramuscular injection and then a sub-cutaneous and an intravenous injection without adjuvant). The serum was collected 15 days after.

Double diffusion on gelose: the serum was studied by double diffusion on gelose according to the OUCH-TERLONY technique.

The biological tests were carried out on the duodenal loop of the $C^3H$ mouse according to the technique of FUJITA and FINKELSTEIN, with 10 mcg of the synthetic sequence in comparison with 10 mcg of purified cholera toxin.

RESULTS:

In vitro: The results obtained in vitro are illustrated in the single accompanying figure which represents the OUCHTERLONY diagram of double diffusion in gelose revealing the strips of precipitation of the toxin and of the antibodies of rabbit serum sensitized with the pentadecapeptide according to the invention, reproducing the sequence 10-24 of the γ chain. According to this diagram, the cholera antitoxin serum contained in the wells 1.7.5. does not recognize the synthetic fragment of too low molecular weight contained in the well 2 (well 1 against 2 and 5 against 2), but recognize the complete toxin contained in the wells 3-4 (wells 1 against 3 and 5 against 4). The serums contained in the wells 6-7 obtained against the synthetic fragment did not give any precipitation strip against the synthetic fragment (7 against 2), on the other hand, one of the serums (7) recognized the sequence of amino acids in the complete toxin (3) (7 against 3). A double diffusion plate of gelose with an identical arrangement with the serums 1,5,6 and 7 before immunization was completely negative.

In vivo: Research of the activity of the synthetic peptide according to the invention, which reproduces a fragment of sub-unit A, has been carried out in the intestinal loop of $C^3H$ mice. The comparative results (measurement of the weight per cm of intestine with respect to a control animal weighing from 60 to 65 mg) are given in milligrams per centimeter of intestine and represent the average of 3 mice per experiment:

(a) after introduction of 10 mcg of cholera toxin (Sigma batch 122 F 0239) into the intestinal loop after 18 hours: 126.7 mg (b) after introduction of 10 mcg of sub-unit B: 67 mg (Sigma batch 12 F 0503)

(c) after introduction of 10 mcg of sub-unit A: 62 mg (Sigma batch 122 F 0240)

(d) after introduction of 10 mcg of sub-unit B (same reference) then after 10 minutes 100 mcg of sub-unit A (same reference): 116.6 mg (e) after introduction of 100 mcg of sub-unit B (same reference) then after 10 minutes 10 mcg of cholera toxin (same reference): 126.7 mg (f) after introduction of 100 mcg of synthetic fragment of sub-unit A: 61 mg (g) after introduction of 10 mcg of sub-unit B (same reference) then after 10 minutes 100 mcg of synthetic fragment of sub-unit A: 63.2 mg (h) after introduction of 100 mcg of sub-unit B +100 mcg of synthetic fragment of sub-unit A, then after 10 minutes 10 mcg of cholera toxin (same reference): 67 mg These results show that the synthetic pentadecapeptide, according to the invention, caused in the rabbit antibodies capable of recognizing, in complete cholera toxin the sequence of A.A. corresponding to the synthetic constituent.

In association with sub-unit B, the pentadecapeptide according to the invention, has inhibited the outflow of water from the tissues by the action of commercial cholera toxin.

The pentadecapeptide according to the invention, played the role of "lure" with respect to the toxin.

Considering the important degree of similarity between the sub-units A of the cholera toxin and of the thermolabile toxin of *Escherichia coli*, this role of lure exists also with respect to toxinogenic *Escherichia coli* and enables to contemplate at the same time a medicinal approach to the treatment of these two diseases and an approach as a diagnosis agent.

The peptide according to the invention, may be used in a pharmaceutically acceptable form, such as solution, powder, etc . . . or also absorbed or coupled in non-covalent manner to a suitable support, in order to permit its liberation slowly and continuously in the patient.

Besides the fact that the synthetic pentadecapeptide according to the present invention enables a protective agent to be available against cholera or against infectious gastro-enterites, or both against one and the other of these diseases, it presents a significant interest from the physiological point of view: the activators of cyclic A.M.P. are, in fact, small in number, so that it permits the elucidation of the mechanisms of action of the biological activities connected with the stimulation of the chain of the cyclic A.M.P. and to contemplate therapeutic treatments of disorders connected with an activation of the adenylcyclase - cyclic A.M.P. system and possibly by coupling or association with an active component such as hormone or any other biological mediator.

Besides its use as a medicament according to the double approach which has just been explained in the foregoing, it is established that the serums obtained by injection of the peptide according to the present invention into rabbits enable the realization of an excellent diagnosis differential of toxinogenic *Escherichia coli* with respect to enteroinvasive *Escherichia coli* and to non-toxinogenic pathogenic *Escherichia coli*. Described below in the first place is a process for the preparation of the serum adapted to be used in the diagnosis test according to the invention, and in the second place, the modalities of production of a diagnosis test using said serum in different biological media.

PREPARATION OF A DIAGNOSIS AGENT ACCORDING TO THE INVENTION

Starting from the synthetic pentadecapeptide whose preparation has been described above, this crystalline synthetic toxin is first dissolved in buffered physiological water in the proportion of 1 mg/ml.

A solution thus prepared is injected as follows into white rabbits weighing 1.8 to 2 kg, shaved on an area 20 cm each side of the spinal column:

First injection: 1 ml of synthetic toxin (1 mg/ml)+1 ml of complete Freund adjuvant mixed at 37° C. 10 intradermal injections of 0.10 ml were made on each side of the spinal column.

Second injection: after 5 days, 1 ml of synthetic toxin is injected by the deep intramuscular route.

Third injection: after 5 days, 1 ml of synthetic toxin is injected subcutaneously.

Fourth injection: after 5 days, 1 ml of the synthetic toxin is injected intravenously.

Fifteen days after the fourth injection, the rabbits were sacrificed. The serum collected was titrated and distributed into ampoules.

DIAGNOSIS TEST

It is carried out:

either on the strain of *E. coli* isolated on gelose 18 hours, or on the stool or on contaminated water in which the presence of *E. coli* is sought.

(A) On the isolated strain

1. At the center of a Petri dish (5 cm diameter) containing 10 ml of Muller-Hinton medium, a culture (in "pastille") of about 1 cm is formed.

2. It is left in the incubator at 30° C. for 18 hours.

3. There is hollowed out to 8 mm of the initial culture of the strain, a well of 8 mm of which the bottom is filled in by a drop of gelose.

4. In the well is placed the synthetic antitoxin serum.

5. There is taken up at the ose a small fragment of the initial culture of the isolated strain for subsequent isolation.

6. The culture is lysed by depositing on the pastille (=culture zone of the strain) two drops of toluene.

7. It is left in contact at the laboratory temperature for 18 hours. The presence of LT toxin of *E. coli* is established by the appearance of a strip of antigen-antibody precipitate at 1 mm from the pastille.

8. The gelose plates are then washed in physiological water, dried between disks of filter paper and dyed with Amidoschwarz.

(B) In water

1. Into a liter of the water to be studied, is added 0.20 ml of magnetic gel beads charged with total anti-*E. Coli* antibodies such as those employed in French Patent Application No. 82 20632 of 9 December 1982; it is left in contact for one hour at 37° C., with stirring if possible.

2. The beads are taken up with a magnetic stick, as described in the aforesaid French Patent Application or by means of the device according to French Patent Application No. 83 17166 of 27 October 1983, they are deposited at the center of a Petri dish containing Muller-Hinton medium.

The sequence of operations is identical with that described at points (A)2. to (A)8. above.

(C) Stools

About 1 g of stools is emulsified in 100 ml of physiological water and the operation is as described in test (B) above.

We claim:

1. Diagnostic agent for the presence of *V. cholerae* and/or toxinogenic *Escherichia coli*, said agent being essentially constituted by a serum taken from rabbits previously treated with injections of the synthetic peptide Gln-Ser-Leu-Gly-Val-Lys-Phe-Leu-Asp-Glu-Tyr-Gln-Ser-Lys-Val.

2. Diagnosis Kit ready-for-use for conducting diagnosis tests enabling the detection of *V. cholerae* and/or toxinogenic *Escherichia coli*, said kit comprising a suitable amount of diagnostic agent for *V. cholerae* and/or *Escherichia coli* and a suitable amount of a reference standard constituted by anti-peptide antibodies where the antibodies are anti-peptide antibodies for the synthetic peptide Gln-Ser-Leu-Gly-Val-Lys-Phe-Leu-Asp-Glu-Tyr-Gln-Ser-Lys-Val and where diagnostic agent is the diagnostic agent of claim 1.

3. Diagnosis Kit ready-for-use for conducting diagnosis tests enabling the detection of *V. cholerae* and/or of toxinogenic *Escherichia coli*, said kit comprising a suitable amount of diagnostic agent for *V. cholerae* and/or *Escherichia coli*, and a suitable amount of a reference standard constituted by anti-peptide antibodies, where the antibodies are anti-peptide antibodies for the synthetic peptide Gln-Ser-Leu-Gly-Val-Lys-Phe-Leu-Asp-Glu-Tyr-Gln-Ser-Lys-Val and where said diagnostic agent is said synthetic peptide.

4. Diagnosis agent for the presence of *V. cholerae* and/or toxinogenic *Escherichia coli*, said agent comprising a serum taken from animals previously treated with injections of the synthetic peptide Gln-Ser-Leu-Gly-Val-Lys-Phe-Leu-Asp-Glu-Tyr-Gln-Ser-Lys-Val.

5. Diagnosis kit ready-for-use for conducting diagnosis tests enabling the detection of *V. cholerae* and/or toxinogenic *Escherichia coli*, said kit comprising a suitable amount of a diagnostic agent for cholera and/or for *Escherichia coli* and suitable amount of a reference standard constituted by anti-peptide antibodies where the antibodies are anti-peptide antibodies for the synthetic peptide Gln-Ser-Leu-Gly-Val-Lys-Phe-Leu-Asp-Glu-Tyr-Gln-Ser-Lys-Val and where the diagnostic agent is the diagnostic agent of claim 4.

6. Diagnosis test for the presence of *V. cholerae* and/or toxinogenic *Escherichia coli*, said test comprising contacting the diagnostic agent according to claim 1 with a biological medium assumed contaminated with the above-said *V. cholerae* and/or toxinogenic *Escherichia coli*, for 16 to 24 hours, after which there appears, if the medium is contaminated, a strip of antigen-antibody precipitate.

* * * * *